(12) United States Patent
Rovatti et al.

(10) Patent No.: US 12,121,640 B2
(45) Date of Patent: Oct. 22, 2024

(54) APPARATUS FOR EXTRACORPOREAL BLOOD TREATMENT

(71) Applicant: GAMBRO LUNDIA AB, Lund (SE)

(72) Inventors: Paolo Rovatti, Modena (IT); Alessandro Surace, Modena (IT); Carlo Alberto Lodi, Modena (IT)

(73) Assignee: Gambro Lundia AB, Lund (SE)

( * ) Notice: Subject to any disclaimer, the term of this patent is extended or adjusted under 35 U.S.C. 154(b) by 533 days.

(21) Appl. No.: 17/418,090

(22) PCT Filed: Dec. 27, 2019

(86) PCT No.: PCT/EP2019/087119
§ 371 (c)(1),
(2) Date: Jun. 24, 2021

(87) PCT Pub. No.: WO2020/136273
PCT Pub. Date: Jul. 2, 2020

(65) Prior Publication Data
US 2022/0096719 A1 Mar. 31, 2022

(30) Foreign Application Priority Data
Dec. 27, 2018 (EP) .................................. 18248086

(51) Int. Cl.
*A61M 1/16* (2006.01)
*A61M 1/34* (2006.01)
(Continued)

(52) U.S. Cl.
CPC ........ *A61M 1/1607* (2014.02); *A61M 1/1609* (2014.02); *A61M 1/1613* (2014.02);
(Continued)

(58) Field of Classification Search
CPC .............. A61M 1/1607; A61M 1/1609; A61M 1/1613; A61M 1/1656; A61M 1/3413;
(Continued)

(56) References Cited

U.S. PATENT DOCUMENTS

| 4,508,622 A | 4/1985 | Polaschegg et al. |
| 5,024,756 A | 6/1991 | Sternby |

(Continued)

OTHER PUBLICATIONS

Chapdelaine et al., "Automated Blood vol. Regulation During Hemodialysis", Progress in Hemodialysis—From Emergent Biotechnology to Clinical Practice, Prof. Angelo Carpi (Ed.), (2011), InTech, Available from: http://www.intechopen.com/books/progress-in-hemodialysis-from-emergent-biotechnology-to-clinicalpractice/automated-blood-volume-regulation-during-hemodialysis.

(Continued)

*Primary Examiner* — Philip R Wiest
(74) *Attorney, Agent, or Firm* — K&L Gates LLP

(57) ABSTRACT

An extracorporeal blood treatment apparatus is provided comprising a filtration unit connected to a blood circuit and to a dialysate circuit, a preparation device for preparing and regulating the composition of the dialysis fluid; a control unit is configured for setting a sodium concentration value for the dialysis fluid in the dialysis supply line at a set point based on the physician prescription; starting from the initial patient plasma conductivity, estimated at the beginning of the treatment, and based on the target plasma conductivity/sodium concentration which is equivalent to the dialysate conductivity/sodium concentration prescribed, the control unit determines the minimum constant gradient between dialysis fluid and plasma conductivity/concentration to be maintained during treatment to achieve the conductivity/concentration target in the patient plasma at the end of the session.

20 Claims, 2 Drawing Sheets

(51) Int. Cl.
*A61M 1/36* (2006.01)
*A61M 60/113* (2021.01)
*A61M 60/279* (2021.01)
*A61M 60/37* (2021.01)
*G16H 10/40* (2018.01)
*G16H 20/40* (2018.01)

(52) U.S. Cl.
CPC ........ *A61M 1/1656* (2013.01); *A61M 1/3413* (2013.01); *A61M 1/3417* (2014.02); *A61M 1/3661* (2014.02); *A61M 60/113* (2021.01); *A61M 60/279* (2021.01); *A61M 60/37* (2021.01); *G16H 10/40* (2018.01); *G16H 20/40* (2018.01); *A61M 2205/3317* (2013.01); *A61M 2205/3334* (2013.01); *A61M 2230/20* (2013.01)

(58) Field of Classification Search
CPC .............. A61M 1/3661; A61M 60/113; A61M 60/279; A61M 60/37; A61M 2205/3317; A61M 2205/3334; A61M 2230/20; G16H 10/40; G16H 20/40
See application file for complete search history.

(56) References Cited

U.S. PATENT DOCUMENTS

| | | |
|---|---|---|
| 6,110,384 A | 8/2000 | Goux et al. |
| 6,123,847 A | 9/2000 | Bene |
| 6,793,827 B1 | 9/2004 | Bosetto et al. |
| 6,881,344 B2 | 4/2005 | Vasta et al. |
| 8,182,692 B2 | 5/2012 | Gotch |
| 9,144,639 B2 | 9/2015 | Vantard et al. |
| 9,943,636 B2 | 4/2018 | Fontanazzi et al. |
| 2012/0018379 A1 | 1/2012 | Gross et al. |
| 2018/0169315 A1 | 6/2018 | Rovatti et al. |

OTHER PUBLICATIONS

Extended European Search Report from European Patent Application No. 18248086.3 mailed Jul. 3, 2019.
International Search Report from International Patent Application No. PCT/EP2019/087119, mailed Mar. 3, 2020.
Written Opinion from International Patent Application No. PCT/EP2019/087119, mailed Mar. 3, 2020.

APPARATUS FOR EXTRACORPOREAL BLOOD TREATMENT

PRIORITY CLAIM

The present application is a National Phase of International Application No. PCT/EP2019/087119, filed Dec. 27, 2019, which claims priority to EP Application No. 18248086.3, filed Dec. 27, 2018. The entire contents of each are incorporated herein by reference and relied upon.

TECHNICAL FIELD

The present invention relates to an apparatus for extracorporeal blood treatment and a method for controlling the extracorporeal blood treatment apparatus.

In particular, the invention may be used for regulating the conductivity of a dialysis liquid during a hemodialysis, or hemodiafiltration treatment.

In more detail, the apparatus and the method are particularly arranged for properly regulating the concentration of sodium in the dialysis liquid, particularly to run an isotonic or an isonatric or an isonatrikalemic dialysis treatment.

BACKGROUND OF THE INVENTION

The kidneys fulfil many functions, including the removal of water, the excretion of catabolites (or waste from the metabolism, for example urea and creatinine), the regulation of the concentration of the electrolytes in the blood (e.g. sodium, potassium, magnesium, calcium, bicarbonates, phosphates, chlorides) and the regulation of the acid/base equilibrium within the body, which is obtained in particular by the removal of weak acids and by the production of ammonium salts.

In individuals who have lost the use of their kidneys, since these excretion and regulation mechanisms no longer work, the body accumulates water and waste from the metabolism and exhibits an excess of electrolytes, as well as, in general, acidosis, the pH of the blood plasma shifting downwards, below 7.35 (the blood pH normally varies within narrow limits of between 7.35 and 7.45). In order to overcome renal dysfunction, resort is conventionally made to a blood treatment involving extracorporeal circulation through an exchanger having a semipermeable membrane (dialyzer) in which the patient's blood is circulated on one side of the membrane and a dialysis liquid, comprising the main electrolytes of the blood in concentrations close to those in the blood of a healthy subject, is circulated on the other side. Furthermore, a pressure difference is created between the two compartments of the dialyzer which are delimited by the semipermeable membrane, so that a fraction of the plasma fluid passes by ultrafiltration through the membrane into the compartment containing the dialysis liquid. The blood treatment which takes place in a dialyzer as regards waste from the metabolism and electrolytes results from two mechanisms of molecular transport through the membrane. On the one hand, the molecules migrate from the liquid where their concentration is higher to the liquid where their concentration is lower. This is diffusive transport. On the other hand, certain catabolites and certain electrolytes are entrained by the plasma fluid which filters through the membrane under the effect of the pressure difference created between the two compartments of the exchanger. This is convective transport.

Three of the abovementioned functions of the kidney, namely the removal of water, the excretion of catabolites and the regulation of the electrolytic concentration of the blood, are therefore performed in a conventional blood treatment device by the combination of dialysis and blood filtration (this combination is referred to as hemodialysis). As regards the regulation of the acid/base equilibrium inside the body, the approach adopted to overcome renal deficiency is to act on a mechanism by which the acid/base equilibrium inside the body is regulated, this mechanism consisting of the buffer systems of the blood, the main one of which comprises carbonic acid, as a weak acid, associated with its alkali salt, bicarbonate. This is why, in order to correct acidosis in a patient suffering from renal insufficiency, he/she is administered with bicarbonate via the vascular route, directly or indirectly, during a hemodialysis session.

Moreover, it must be underlined that sodium is the main ionic solute of extracellular volume. From literature search and according to the main opinion leaders in the dialysis field, the determination of dialysis fluid sodium concentration to be used during the dialysis treatment appears as one of the major challenges of dialysis prescription. The dialysis fluid sodium concentration significantly affects the sodium balance and the intracellular hydration of the patient with implications on hemodialysis tolerance and also long term patient survival. Hypertonic dialysis fluid sodium prescription will result in a positive sodium balance followed by a water shift from the intracellular to extracellular compartment. The intracellular dehydration increases vasopressin release and provokes thirst with the consequence of a greater inter-dialytic weight gain and hypertension. On the contrary, a dialysis fluid sodium concentration that is too low (i.e., hypotonic) will provoke a negative sodium gradient with a water shift in the intracellular compartment, which is responsible for intra-dialytic cramps, headache, hypovolemia and risk of hypotension. One of current opinions is the idea that sodium balance should be maintained null during a dialysis treatment: this is based on the so-called "sodium set point" theory, according to which both healthy subjects and dialysis patients tend to maintain a stable extra-cellular sodium concentration. In this hemodialysis method, referred to as "isonatric dialysis", plasma sodium concentration should be identical through the entire dialysis session. On a dialysis machine, where the direct measure and control of plasma sodium concentration is not possible, there is the need to use the entire conductivity (measured by sensors or estimated through software monitoring systems as Diascan®): in this case is more correct to talk about "isotonic dialysis". This hypothesis of work is still valid since sodium is the major contributor in the plasma conductivity. As above mentioned, sodium is removed during dialysis through convection and diffusion. The main sodium removal process during dialysis is convective. If we assume that the ultrafiltrate fluid is basically isotonic, convection does not change the tonicity of the extracellular fluid. However, the isotonic/isonatric dialysis may not be the best treatment type for all the patients. Patients with a too low initial sodium concentration may need a positive sodium gradient to sustain vascular refilling during the session, whereas patients with critical hypertension need to loose sodium during the treatment with a negative sodium gradient. The sodium gradient is defined as the difference between dialysate and plasma sodium concentrations. In the present situation, there is a need to help the physician to prescribe a "physiological" dialysis fluid composition to treat the patient. Moreover, a second need is to have a bio-sensing-based therapy which is easy to use and designed also for operators not very skilled or working in crowded and very busy dialysis rooms. To at least partly solve the above mentioned drawbacks, document U.S. Pat. No. 4,508,622 teaches a dialysis device in which the electrolyte composition of the untreated and treated fluids routed through the dialyzer may be determined and the composition of the dialysis solution adapted to the patient's requirements. A first electrolyte detector (conductivity cell) is provided upstream of the dialyzer and a second electrolyte detector (conductivity cell) is provided downstream of the dialyzer. Each detector is coupled to a readout element through which both of the values of the dialysis solution may be observed and eventually controlled. In more detail, the apparatus according to U.S. Pat. No. 4,508,622 consists essentially of a unit for production of the dialysis solution and a dialyzer connected to the unit and followed downstream by a pump to produce a vacuum in the dialyzer on the side of the dialysis fluid. The detector mounted upstream of the dialyzer, and connected with a control unit, measures the conductivity of the total dialysis solution. A second detector is mounted downstream of dialyzer and is connected with a comparator which is, in turn, connected to a differentiation unit. A control signal is provided by the differentiation unit to control unit if there is a difference in the differentiation unit that deviates from the predetermined nominal value. During dialysis fluid circulation, if detector generates a signal to the evaluation unit and subsequently to the differentiation unit which deviates by a certain amount from the signal generated by detector, i.e., a difference in value appears which deviates from the predetermined value for differentiation unit, the difference unit activates the control unit, which in turn switches concentrate pump on or off as a function of the higher or lower concentration in the dialysis solution to be produced. A treatment in which the dialysis fluid has the same conductivity of the blood and of the spent dialysis fluid, is one of the described implementations. However, the dialysis fluid and the blood reach the same conductivity after a certain time lapse which clearly affects the pre-dialytic plasma sodium content. Therefore, the method described in U.S. Pat. No. 4,508,622 in not properly an 'isoconductive' dialysis treatment. In any case, 'isoconductive' dialysis has been shown to lead to undesired sodium loading in the patient. Moreover, the prior art devices include dialysis apparatus wherein the conductivity of dialysis fluid is controlled in order to reach a desired post-dialysis plasmatic conductivity, i.e. conductivity (or sodium concentration) of the patient's blood at the end of the dialysis treatment.

It is known, for example from EP 1389475, a dialysis apparatus provided with a conductivity system that computes the dialysis fluid conductivity (corresponding to the dialysis fluid sodium concentration) from periodic measurements of the sodium blood concentration allowing the sodium level of the patient to reach a prescribed end-of-session value. This dialysis apparatus includes a bag and a pump for infusing a patient with an infusion solution containing sodium at a determined and known concentration. A structure for determining the sodium concentration $[Na^+]_{dial}$ of the dialysis liquid is also provided so that the patient's body tends towards a desired sodium concentration $[Na^+]_{des}$, as a function of the dialysance D for sodium of the dialyzer, of the desired sodium concentration $[Na^+]_{des}$ inside the patient's body, of the infusion flow rate and of the sodium concentration $[Na^+]_{sol}$ of the infusion solution. A control unit drives the pump for regulating the sodium concentration of the dialysis liquid such that this concentration is equal (tends towards) to the determined concentration $[Na^+]_{dial}$.

As previously mentioned, the problems of the dialysis apparatus of the discussed prior art are presently both the choice of the appropriate post-dialysis plasmatic conductivity target and a proper algorithm control to minimize side effects of sodium concentration difference between the dialysis fluid and the patient blood.

EP 2377563 discloses a dialysis apparatus comprising a blood treatment unit with an online preparation device for preparing a dialysis fluid containing sodium and comprising a dialysis preparation section for regulating the concentration of sodium in the dialysis fluid. The blood circuit is configured to circulate extracorporeal blood through the blood chamber; control means determines a value representative of the sodium concentration in the blood and are programmed for driving the dialysis preparation section as a function of the determined plasma sodium value, such that the substance concentration in the dialysis fluid tends towards the substance concentration in the blood. The plasma sodium content is determined by measuring the inlet and outlet conductivities of the dialysis fluid upstream and downstream the dialyzer, by then changing the conductivity upstream the filter by a prefixed step and measuring a second time the inlet and outlet conductivities of the dialysis fluid upstream and downstream the dialyzer with the modified conductivity value. With the methods described, for example in EP 547025 or in EP 920877, it is possible to determine the plasma conductivity and thereby to properly regulate the dialysis fluid preparation section.

The described system however changes the blood conductivity and tonicity since the dialysis fluid enters into contact and exchange significantly with blood before a plasma conductivity calculation; the effect on plasma conductivity is in an amount proportional to the difference between blood and dialysis fluid conductivities. Finally, document U.S. Pat. No. 8,182,692 describes a dialysis apparatus providing a treatment in which a dialysis fluid having a sodium concentration substantially equal to the estimated current sodium concentration in the patient's blood is performed by placing the dialysis fluid in communication with the patient's blood across the semi-permeable membrane to perform a dialysis treatment on the patient's blood without substantially altering the sodium concentration of the patient's blood during the performance of the dialysis treatment. In more detail, a solution supply device, containing a conductivity-testing solution, is selectively placed in communication with dialyzer and the blood flowing therein. According to this patent, any subject, including hemodialysis patients, has a set level of sodium in his body, referred to as the "set point." The set point of a subject tends to remain relatively constant, and sodium levels deviating too far from the set point may cause discomfort to the subject. Given the above, the method of the prior art includes causing blood to flow through blood conduit of the dialyzer and flowing the conductivity-testing solution in the opposite direction through the dialyzer. Conductivity detectors measure the conductivity of conductivity-testing solution as the solution enters and exits dialyzer. Conductivity-testing solution is formulated such that electrically conductive solutes other than sodium in the patient's blood have little or no effect on the conductivity measurements of conductivity-testing solution. According to U.S. Pat. No. 8,182,692, due to the closely matched concentrations of electrically conductive solutes, such as phosphate, sulfate, bicarbonate, potassium, calcium, and magnesium, in conductivity-testing solution and in the patient's blood, little diffusion of those electrically conductive solutes occurs across membrane. Consequently, the conductivity measurements of conductivity-testing solution is closely correlated with the level of sodium in the patient's blood. Therefore, conductivity-testing solution is exclusively used to accurately determine the level of sodium in the patient's blood as a function of the change in conductivity across dialyzer of the conductivity-testing solution.

Control unit then determines the level of sodium in the patient's blood as a function of the measured conductivity values. After determining the concentration of sodium in the patient's blood, dialysis fluid may be prepared to include a concentration of sodium that is substantially equal to the concentration of sodium determined to exist in the patient's blood. Moreover, US2012/018379 discloses an apparatus and a method for the determination and regulation of the concentration of one dissolved substance (e.g. sodium) in a dialysis fluid circuit of a hemodialysis machine. The user presets the sodium regulation range before the start of the dialysis using an estimated value for the dialysis fluid sodium required to achieve the isonatric state or a lab measurement of the patient sodium or a value determined by the regulation from earlier treatments. In addition, the distribution volume of the patient is input for the application of the model for the correction of the diffusive balance. Furthermore, the initial concentrations of bicarbonate and potassium in the patient are set. They come from an analysis with a blood gas analyzer before the start of the dialysis treatment. After the start of the treatment, the dialysis fluid flow and the conductivity are determined upstream and downstream of the dialyzer and a calculation of the updated current bicarbonate and potassium concentration in the patient takes place with it being assumed that the potassium clearance corresponds to the sodium clearance and that the bicarbonate clearance corresponds to 70% of the sodium clearance. The sodium clearance from the blood flow is estimated until the presence of the first clearance measurement. The calculation of the conductivity balance and of the correction term for the ion exchange and thus for the sodium balance then takes place from these data. The conductivity of fluids measured upstream and downstream, the sodium balance and the correction term for the dialysate conductivity downstream of the dialyzer are then the input values for the sodium regulation. The desired conductivity thus determined is finally converted into a desired value for the dialysis fluid sodium while taking account of the composition of the dialysis concentrate and this preset value is transmitted to a metering unit for dialysis fluid preparation.

Document US20180169315 discloses an extracorporeal blood treatment apparatus with a filtration unit connected to a blood circuit and to a dialysate circuit. The apparatus further comprises a preparation device for preparing and regulating the composition of the dialysis fluid, and a sensor for measuring conductivity of the dialysate (i.e. spent dialysis fluid); a control unit is configured for setting a sodium concentration in the dialysis fluid and after setting the dialysis fluid at the initial set point, circulating the dialysis fluid and blood through the filtration unit, measuring an initial conductivity value of the dialysate at the beginning of the treatment, and calculating, based on the measured initial conductivity value of the spent dialysis fluid and on the corresponding conductivity value of the dialysis fluid, the value of the initial plasma conductivity; the step of circulating the dialysis fluid up to the calculating of the initial plasma conductivity is performed maintaining the dialysis fluid conductivity substantially constant.

SUMMARY

An aim of the present invention is providing an extracorporeal blood treatment apparatus able to automatically perform a proper setting of the dialysis fluid content of a substance, particularly an ionic substance, present in the blood as well. In detail it is an aim of the present invention to provide an extracorporeal blood treatment apparatus with a proper tool helping the physician to prescribe a "physiological" dialysis fluid composition, particularly to run an isotonic, isonatric or a dialysis treatment with positive/negative sodium gradients. It is an object to provide an extracorporeal blood treatment apparatus configured to run a dialysis treatment avoiding changes in prescription parameters and continuing to work with safe clinical conditions regardless of the type of treatment chosen. A further aim of the invention is to make available an extracorporeal blood treatment apparatus provided with a selectable biosensing-based therapy which is easy to use and designed for not skilled operators or users working in crowded and busy dialysis rooms. It is an object to provide an extracorporeal blood treatment apparatus configured to run a dialysis treatment in any of hemodialysis (HD) and hemodiafiltration (HDF) treatment modes. It is an aim of the invention to provide an extracorporeal blood treatment machine configured to automatically perform a proper automatic setting of the dialysis fluid conductivity. A further aim of the invention is to make available a dialysis apparatus able to provide an automated delivery and control of the dialysis prescription, particularly in order to restore at each dialysis session the proper sodium-water equilibrium to the patient. At least one of the above-indicated aims is attained by an apparatus and a corresponding method as in one or more of the appended claims, taken singly or in any combination.

According to a first independent aspect of the invention an extracorporeal blood treatment device is provided including:
- a filtration unit (2) having a primary chamber (3) and a secondary chamber (4) separated by a semi-permeable membrane (5);
- a blood circuit including a blood withdrawal line (6) connected to an inlet of the primary chamber (3) and a blood return line (7) connected to an outlet of the primary chamber (3), said blood lines being configured for connection to a patient cardiovascular system;
- a dialysis supply line (8) connected to an inlet of the secondary chamber (4);
- a dialysis effluent line (13) connected to an outlet of the secondary chamber (4);
- a preparation device (9) for preparing a dialysis fluid connected to said dialysis supply line (8) and comprising regulating means (10) for regulating the composition of the dialysis fluid,
- a sensor (11) for measuring a parameter value of a dialysate in the dialysis effluent line (13), said parameter of the dialysate being at least one chosen in a group consisting of conductivity of the dialysate and a concentration of at least a substance in the dialysate;
- a control unit (12) connected to the regulating means (10), connected to the sensor (11) for receiving said parameter value of the dialysate and configured for:
    setting a parameter value for the dialysis fluid in the dialysis supply line (8) at an initial set point, said parameter of the dialysis fluid being at least one chosen in a group consisting of conductivity of the dialysis fluid and a concentration of at least a substance in the dialysis fluid;
    after setting the dialysis fluid parameter value at the initial set point, circulating the dialysis fluid through the secondary chamber (4) of the filtration unit (2);
    circulating blood through the primary chamber (3) of the filtration unit (2);

measuring values of said parameter of the dialysate downstream of said secondary chamber (4), determining, by receiving, measuring or calculating, a parameter relating to the efficiency of the filtration unit (2);

determining, by receiving, measuring or calculating, a plasma conductivity or a plasma concentration of at least a substance in the blood;

calculating an updated value of the parameter for the dialysis fluid in the dialysis supply line (8) based on the parameter value of a dialysate in the dialysis effluent line (13), the parameter relating to the efficiency of the filtration unit (2) and a gradient between a current value of the parameter value for the dialysis fluid in the dialysis supply line (8) and the plasma conductivity or the plasma concentration of at least a substance in the blood, wherein calculating the updated value includes keeping the gradient substantially constant.

In a further independent aspect a method for setting parameters in an apparatus for extracorporeal blood treatment is provided, the apparatus comprising:

a filtration unit (2) having a primary chamber (3) and a secondary chamber (4) separated by a semi-permeable membrane (5);

a blood withdrawal line (6) connected to an inlet of the primary chamber (3);

a blood return line (7) connected to an outlet of the primary chamber (3), said blood lines being configured for connection to a patient cardiovascular system;

a dialysis supply line (8) connected to an inlet of the secondary chamber (4);

a dialysis effluent line (13) connected to an outlet of the secondary chamber (4);

a preparation device (9) for preparing a dialysis fluid connected to said supply line (2) and comprising regulating means (10) for regulating the composition of the dialysis fluid;

a sensor (11) for measuring a parameter value of a dialysate in the dialysis effluent line (13), said parameter of the dialysate being at least one chosen in a group consisting of conductivity of the dialysate and a concentration of at least a substance in the dialysate;

a control unit (12) connected to the regulating means (10), connected to the sensor (11) for receiving said parameter value of the dialysate, the method comprising the following steps performed by the control unit:

setting a parameter value for the dialysis fluid in the dialysis supply line (8) at an initial set point, said parameter of the dialysis fluid being at least one chosen in a group consisting of conductivity of the dialysis fluid and a concentration of at least a substance in the dialysis fluid;

after setting the dialysis fluid parameter value at the initial set point, circulating the dialysis fluid through the secondary chamber (4) of the filtration unit (2);

circulating blood through the primary chamber (3) of the filtration unit (2);

measuring values of said parameter of the dialysate downstream of said secondary chamber (4), determining, by receiving, measuring or calculating, a parameter relating to the efficiency of the filtration unit (2);

determining, by receiving, measuring or calculating, a plasma conductivity or a plasma concentration of at least a substance in the blood;

calculating an updated value of the parameter for the dialysis fluid in the dialysis supply line (8) based on the parameter value of a dialysate in the dialysis effluent line (13), the parameter relating to the efficiency of the filtration unit (2) and a gradient between a current value of the parameter value for the dialysis fluid in the dialysis supply line (8) and the plasma conductivity or the plasma concentration of at least a substance in the blood, wherein calculating the updated value includes keeping the gradient substantially constant.

The following aspects refer both to the apparatus and to the method.

In a 2$^{nd}$ aspect according to anyone of the previous aspects, the control unit is configured for calculating the updated value of the parameter for the dialysis fluid in the dialysis supply line (8) based on a dialysate flow rate, in particular the dialysate flow rate at filtration unit inlet.

In a 3$^{rd}$ aspect according to anyone of the previous aspects, the control unit (12) is configured for calculating the updated value of the parameter for the dialysis fluid in the dialysis supply line (8) based on a weight loss rate (or based on an ultrafiltration flow rate) through the filtration unit.

In a 4$^{th}$ aspect according to anyone of the previous aspects, the control unit (12) is configured for calculating the updated value of the parameter for the dialysis fluid in the dialysis supply line (8) based on the sum of a dialysate flow rate (particularly at filtration unit inlet) and a weight loss rate through the filtration unit (2).

In a 5$^{th}$ aspect according to anyone of the previous aspects, the control unit (12) is configured for calculating the updated value of the parameter for the dialysis fluid in the dialysis supply line (8) based on a dialysate flow rate at filtration unit outlet.

In a 6$^{th}$ aspect according to anyone of the previous aspects, wherein the gradient is defined as follows:

$$\Delta=(c_{di}-c_{bi})$$

or $$\Delta=(\kappa_{di}-\kappa_{bi})$$

wherein $c_{di}$ is the concentration of at least a substance in the dialysis fluid at the inlet of the filtration unit;

$c_{bi}$ is the concentration of at least a substance in the blood;

$\kappa_{di}$ is the conductivity of the dialysis fluid at the inlet of the filtration unit;

$\kappa_{bi}$ is the plasma conductivity;

the gradient being defined either by a difference between conductivities or by a difference in concentrations.

In a 7$^{th}$ aspect according to anyone of the previous aspects, wherein said substance in the blood is a ionic substance, in particular sodium.

In a 8$^{th}$ aspect according to anyone of the previous aspects, wherein said substance in the dialysis fluid in the dialysis supply line (8) is a ionic substance, in particular sodium.

In a 9$^{th}$ aspect according to anyone of the previous aspects, said substance in the dialysate in the dialysis effluent line (13) is a ionic substance, in particular sodium.

In a 10$^{th}$ aspect according to anyone of the previous aspects, the parameter relating to the efficiency of the filtration unit (2) is the clearance or the dialysance of the filtration unit (2), in particular the ionic dialysance.

In a 11$^{th}$ aspect according to anyone of the previous aspects, the control unit is configured to calculate the updated value of the parameter for the dialysis fluid in the dialysis supply line (8) based on a sum of two terms, a first term including the parameter value of a dialysate in the dialysis effluent line (13) and a second term including the parameter relating to the efficiency of the filtration unit (2) and the gradient.

In a 12$^{th}$ aspect according to the previous aspect, the second term includes one or more of a dialysate flow rate at filtration unit inlet, an ultrafiltration flow rate through the filtration unit and a dialysate flow rate at filtration unit outlet.

In a 13$^{th}$ aspect according to anyone of the previous two aspects, the first term is proportional to the parameter value of a dialysate in the dialysis effluent line (13) and in particular is the parameter value of a dialysate in the dialysis effluent line (13).

In a 14$^{th}$ aspect according to anyone of the previous three aspects, the second term is proportional to both the parameter relating to the efficiency of the filtration unit (2) and the gradient.

In a 15$^{th}$ aspect according to anyone of the previous four aspects, the second term is inversely proportional to at least one of a dialysate flow rate at filtration unit inlet, an ultrafiltration flow rate through the filtration unit and a dialysate flow rate at filtration unit outlet, in particular the second term being inversely proportional to either the dialysate flow rate at filtration unit outlet or to the sum of the dialysate flow rate at filtration unit inlet and the ultrafiltration flow rate through the filtration unit.

In a 16$^{th}$ aspect according to anyone of the previous aspects, the control unit is configured to calculate the updated value of the parameter for the dialysis fluid in the dialysis supply line (8) based on the $$c_{di} = c_{do} + \frac{\Delta \cdot D}{Q_d + Q_{wl}}$$

or $$\kappa_{di} = \kappa_{do} + \frac{\Delta \cdot D}{Q_d + Q_{wl}}$$

wherein $c_{di}$ is the concentration of at least a substance in the dialysis fluid at the inlet of the filtration unit;

$c_{do}$ is the concentration of at least a substance in the dialysate at the outlet of the filtration unit;

$\kappa_{di}$ is the conductivity of the dialysis fluid at the inlet of the filtration unit;

$\kappa_{do}$ is the conductivity of the dialysate at the outlet of the filtration unit;

$\Delta$ is the gradient;

D is the parameter relating to the efficiency of the filtration unit (2);

$Q_d$ is the dialysate flow rate;

$Q_{wl}$ is the weight loss rate.

In a 17$^{th}$ aspect according to anyone of the previous aspects, the control unit is configured to calculate the updated value of the parameter for the dialysis fluid in the dialysis supply line (8) based on the following formula:

$$c_{di} = c_{do} + \frac{\Delta \cdot D}{Q_{do}}$$

or $$\kappa_{di} = \kappa_{do} + \frac{\Delta \cdot D}{Q_{do}}$$

wherein $c_{di}$ is the concentration of at least a substance in the dialysis fluid at the inlet of the filtration unit;

$c_{do}$ is the concentration of at least a substance in the dialysate at the outlet of the filtration unit;

$\kappa_{di}$ is the conductivity of the dialysis fluid at the inlet of the filtration unit;

$\kappa_{do}$ is the conductivity of the dialysate at the outlet of the filtration unit;

$\Delta$ is the gradient;

D is the parameter relating to the efficiency of the filtration unit (2);

$Q_{do}$ is the dialysate flow rate at filtration unit outlet.

In a 18$^{th}$ aspect according to anyone of the previous aspects, the control unit is configured to receive as input the initial set point of the parameter value for the dialysis fluid in the dialysis supply line (8), the control unit determining the gradient value in order to achieve a value of the plasma conductivity or of the plasma concentration of at least a substance in the blood at the end of the treatment tending to, or coincident with, the initial set point of the parameter value.

In a 19$^{th}$ aspect according to anyone of the previous aspects, the gradient is determined iteratively.

In a 20$^{th}$ aspect according to anyone of the previous aspects, wherein the control unit is configured to receive as input a desired value of the plasma conductivity or of the plasma concentration of at least a substance in the blood to be reached at the end of the treatment, the control unit determining the gradient value in order to achieve the desired value of the plasma conductivity or the plasma concentration of at least a substance in the blood at the end of the treatment.

In a 21$^{st}$ aspect according to anyone of the previous aspects, the regulating means (10) modify the dialysis fluid composition by changing conductivity of the dialysis fluid and/or by changing the concentration of at least one substance in the dialysis fluid and wherein the preparation device (9) prepares a dialysis fluid containing at least a substance, said substance being present in the blood too, said regulating means (10) regulating the concentration of at least said substance in the dialysis fluid, in particular said substance being sodium.

In a 22$^{nd}$ aspect according to anyone of the previous aspects, wherein the control unit (12) is configured to determine at least a conductivity of the dialysis fluid upstream said secondary chamber (4), said determining being executed either by receiving the dialysis fluid conductivity current set value or by receiving a signal from a sensor for measuring a conductivity-related value of the dialysis fluid in the dialysis fluid supply line (8).

In a 23$^{rd}$ aspect according to anyone of the previous aspects, the control unit is configured to calculate the plasma conductivity as a function of the dialysate flow rate at the outlet of the secondary chamber (4), and/or wherein the control unit is configured to calculate the plasma conductivity as a function of the blood flow rate in the blood lines (6, 7).

In a 24$^{th}$ aspect according to anyone of the previous aspects, the control unit is configured to calculate the plasma conductivity as a function of at least an efficiency parameter of the filtration unit (2), in particular a clearance of the filtration unit (2), optionally the urea clearance.

In a 25$^{th}$ aspect according to anyone of the previous aspects, the control unit is configured to calculate the plasma conductivity as a function of at least an initial conductivity of the dialysate and a conductivity of the dialysis fluid in the dialysis supply line (8).

In a 26$^{th}$ aspect according to anyone of the previous aspects, the control unit is configured to calculate the plasma conductivity according to the following formula:

$$\kappa_p = \kappa_{do} + \frac{Q_{do}}{Q_{bset}}(\kappa_{do} - \kappa_{di})$$

wherein:

| | |
|---|---|
| $\kappa_p$ | plasma conductivity; |
| $Q_{do}$ | Dialysate flow rate at the filtration unit outlet; |
| $Q_{bset}$ | Set blood flow rate at the filtration unit inlet; |
| $k_{di}$ | Dialysis fluid conductivity at the filtration unit inlet; |
| $k_{do}$ | Dialysate conductivity at the filtration unit outlet; |

In a 27$^{th}$ aspect according to anyone of the previous aspects, the control unit is configured to calculate the plasma conductivity according to the following formula:

$$\kappa_p = \kappa_{do} + \frac{Q_{do}}{K_u}(\kappa_{do} - \kappa_{di})$$

wherein:

| | |
|---|---|
| $\kappa_p$ | plasma conductivity; |
| $Q_{do}$ | Dialysate fluid flow rate at the filtration unit outlet; |
| $K_u$ | Filtration unit clearance for urea; |
| $k_{di}$ | Dialysis fluid conductivity at the filtration unit inlet; |
| $k_{do}$ | Dialysate conductivity at the filtration unit outlet; |

In a 28$^{th}$ aspect according to anyone of the previous aspects, after calculating the initial plasma conductivity, the control unit is configured to drive the regulating means (10) to change the composition of the dialysis fluid to reach a dialysis fluid conductivity substantially equal to the calculated initial plasma conductivity.

In a 29$^{th}$ aspect according to the previous aspect, after setting the dialysis fluid conductivity substantially equal to the calculated plasma conductivity, the control unit is configured to execute a second calculating step, based on a second determined initial conductivity of the dialysate and on a second corresponding conductivity of the dialysis fluid in the supply line (8), of a second estimate of the initial plasma conductivity, said calculating the second estimate being performed maintaining the dialysis fluid conductivity substantially constant and substantially equal to the calculated plasma conductivity.

In a 30$^{th}$ aspect according to the previous aspect, after calculating the second estimate of the initial plasma conductivity, the control unit is configured to use said second estimate to calculate the updated value of the parameter for the dialysis fluid in the dialysis supply line (8).

In a 31$^{st}$ aspect according to anyone of the previous aspects, the parameter of the dialysis fluid is the conductivity of the dialysis fluid, or the concentration of at least a substance in the dialysis fluid, said substance being in particular sodium.

In a 32$^{nd}$ aspect according to anyone of the previous aspects, the control unit (12) determines, by receiving, measuring or calculating, the plasma conductivity and the parameter of the dialysis fluid is the conductivity of the dialysis fluid.

In a 33$^{rd}$ aspect according to anyone of the previous aspects, the control unit (12) determines, by receiving, measuring or calculating, the concentration of at least a substance in the blood, said substance being in particular sodium, and wherein the parameter of the dialysis fluid is the concentration of at least a substance in the dialysis fluid, said substance being in particular sodium.

In a 34th aspect according to anyone of the previous aspects, the control unit (12) determines, by receiving, measuring or calculating, the concentration of at least a substance in the blood, and wherein the parameter of the dialysis fluid is the concentration of at least the same substance in the dialysis fluid.

In a 35$^{th}$ aspect according to anyone of the previous aspects, the control unit drives the regulating means (10) for regulating the conductivity or the concentration of at least a substance in the dialysis fluid, the control unit setting the parameter value for the dialysis fluid in the dialysis supply line (8) at the updated value.

In a 36$^{th}$ aspect according to the previous aspect, the regulating means (10) regulates the concentration of at least a substance in the dialysis fluid, in particular an ionic substance, such as sodium.

In a 37$^{th}$ aspect according to the previous aspect, the control unit drives the regulating means (10) for regulating the sodium concentration in the dialysis fluid to set the parameter value for the dialysis fluid in the dialysis supply line (8) at the updated value.

In a 38$^{th}$ aspect according to anyone of the previous aspects, the control unit (12) is programmed for calculating said plasma conductivity or said plasma concentration of at least a substance in the blood.

In a 39$^{th}$ aspect according to anyone of the previous aspects, the control unit (12) is programmed for receiving as an input said plasma conductivity or said plasma concentration of at least a substance in the blood.

In a 40$^{th}$ aspect according to anyone of the previous aspects, the control unit (12) is programmed for storing in a memory a value of said plasma conductivity or of said plasma concentration of at least a substance in the blood, said value representative of a parameter of the blood being not calculated by the control unit.

In a 41$^{st}$ aspect according to anyone of the previous aspects, the control unit is configured to calculate the plasma conductivity as a function of at least one flow rate, in particular said flow rate being chosen in the group including the dialysate flow rate at the outlet of the secondary chamber (4) and the blood flow rate in the blood lines (6, 7).

In a 42$^{nd}$ aspect according to anyone of the previous aspects, the control unit is configured to calculate the plasma conductivity as a function of at least an initial conductivity of the dialysate.

In a 43$^{rd}$ aspect according to anyone of the previous aspects, the control unit is configured to calculate the plasma conductivity as a function of at least a conductivity of the dialysis fluid in the dialysis supply line (8).

In a 44$^{th}$ aspect according to anyone of the previous aspects, the control unit is programmed to allow selection of at least one treatment mode chosen in the group including HD and HDF treatment mode and to optionally allow selection between isotonic dialysis with gradient equal to zero or non-isotonic dialysis with gradient different from zero.

In a $45^{th}$ aspect according to anyone of the previous aspects, the control unit is configured to drive the regulating means to set the parameter value for the dialysis fluid in the dialysis supply line (8) at the initial set point and to calculate the updated value of the parameter for the dialysis fluid in the dialysis supply line (8) as a function of the gradient, the control unit is further configured subsequently to drive the regulating means as a function of the gradient to set the parameter value for the dialysis fluid in the dialysis supply line (8) at the updated value.

In a $46^{th}$ aspect according to anyone of the previous aspects, the control unit (12) is configured for determining, particularly calculating, the plasma conductivity or the plasma concentration of at least a substance in the blood a plurality of times during the treatment, an updated value of the parameter for the dialysis fluid in the dialysis supply line (8) being calculated when the plasma conductivity or the plasma concentration is newly determined during the treatment. Calculating the updated value includes keeping the gradient substantially constant.

In a $47^{th}$ aspect according to anyone of the previous aspects, the control unit (12) is configured for determining, particularly calculating, the parameter relating to the efficiency of the filtration unit (2), an updated value of the parameter for the dialysis fluid in the dialysis supply line (8) being calculated when the parameter relating to the efficiency of the filtration unit (2) is newly determined during the treatment. Calculating the updated value includes keeping the gradient substantially constant.

In a $48^{th}$ aspect according to anyone of the previous aspects, the control unit (12) is further configured, during a monitoring phase, to re-determine the plasma conductivity or the plasma concentration of at least a substance in the blood, the monitoring phase occurring a predetermined number of times during the treatment, at each monitoring phase an updated value of the parameter for the dialysis fluid in the dialysis supply line (8) being calculated.

In a $49^{th}$ aspect according to anyone of the previous aspects, the regulating means (10) regulates the concentration of the substance in the dialysis fluid, in particular an ionic substance, such as sodium.

In a $50^{th}$ aspect according to anyone of the previous aspects, the control unit is programmed to check whether the calculated plasma conductivity is within an acceptable safety range.

In a $51^{st}$ aspect according to anyone of the previous aspects, the control unit is configured to propose the updated value of the parameter for the dialysis fluid to the user and to request confirmation prior driving the regulating means (10) for regulating the sodium concentration in the dialysis fluid to set the parameter value for the dialysis fluid in the dialysis supply line (8) at the updated value.

In a $52^{nd}$ aspect according to anyone of the previous aspects, the control unit is configured to automatically set the updated value of the parameter for the dialysis fluid and to drive the regulating means (10) for regulating the sodium concentration in the dialysis fluid to set the parameter value for the dialysis fluid in the dialysis supply line (8) at the updated value.

In a $53^{rd}$ aspect according to anyone of the previous aspects, the control unit is configured to calculate the plasma conductivity or the plasma concentration at least from measured values of said parameter of the dialysate in the dialysis effluent line (13).

In a $54^{th}$ aspect according to anyone of the previous aspects, the control unit is configured to calculate the plasma conductivity or the plasma concentration at least from values, in particular measured values, of said parameter of the dialysis fluid in the dialysis supply line (8) and from measured values of said parameter of the dialysate in the dialysis effluent line (13).

In a $55^{th}$ aspect according to anyone of the previous aspects, the control unit is configured to calculate the plasma conductivity or the plasma concentration from at least two parameter values of the dialysis fluid and of the dialysate determined respectively upstream and downstream of said filtration unit (2) in at least two successively prepared dialysis fluids with different concentrations of a substance, in particular a ionic substance, for example sodium, said control unit (12) being in particular programmed for performing said calculation at least twice, and more in detail a plurality of times, and at predetermined times during a dialysis treatment.

In a $56^{th}$ aspect according to anyone of the previous aspects, the control unit is configured to calculate the parameter relating to the efficiency of the filtration unit (2) at least from measured values of said parameter of the dialysate in the dialysis effluent line (13).

In a $57^{th}$ aspect according to anyone of the previous aspects, the control unit is configured to calculate the parameter relating to the efficiency of the filtration unit (2) at least from values, in particular measured values, of said parameter of the dialysis fluid in the dialysis supply line (8) and from measured values of said parameter of the dialysate in the dialysis effluent line (13).

In a $58^{th}$ aspect according to anyone of the previous aspects, the control unit is configured to calculate the parameter relating to the efficiency of the filtration unit (2) from at least two parameter values of the dialysis fluid and of the dialysate determined respectively upstream and downstream of said filtration unit (2) in at least two successively prepared dialysis fluids with different concentrations of a substance, in particular a ionic substance, for example sodium, said control unit (12) being in particular programmed for performing said calculation at least twice, and more in detail a plurality of times, and at predetermined times during a dialysis treatment.

Further characteristics and advantages of the present invention will better emerge from the detailed description that follows of at least an embodiment of the invention, illustrated by way of non-limiting example in the accompanying figures of the drawings.

BRIEF DESCRIPTION OF THE DRAWINGS

The description will now follow, with reference to the appended figures, provided by way of non-limiting example, in which.

DETAILED DESCRIPTION

Blood Treatment Apparatus

Figure 1:
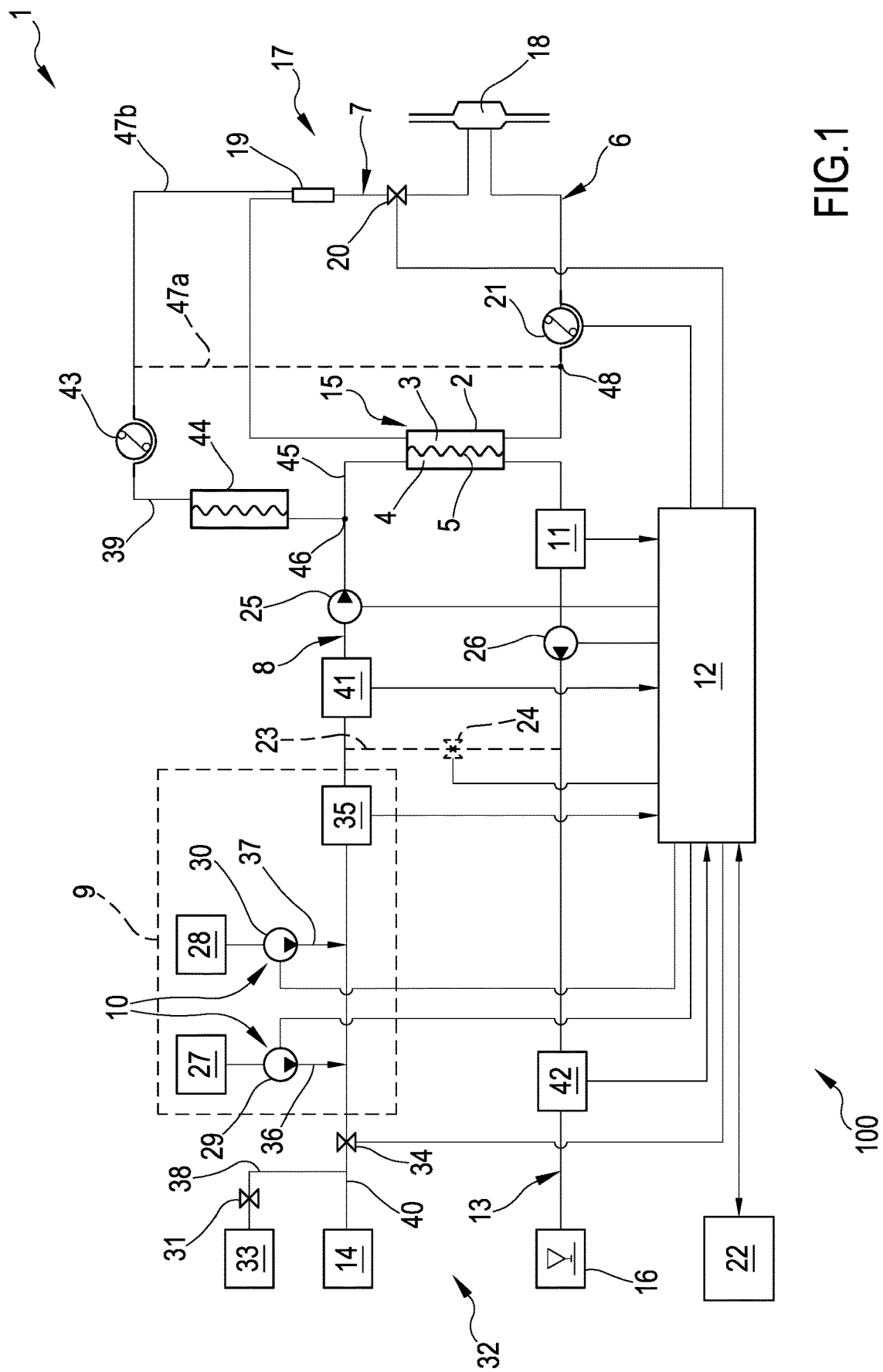
FIG. 1 schematically represents an extracorporeal blood treatment apparatus made according to an illustrating embodiment.

FIG. 1 illustrates an extracorporeal blood treatment apparatus 1 in an embodiment of the invention. An example of a hydraulic circuit 100 is schematically illustrated, but it is to be noted that the specific structure of the hydraulic circuit 100 is not relevant for the purposes of the present invention and therefore other and different circuits to those specifically shown in FIG. 1 might be used in consequence of the functional and design needs of each single medical apparatus. The hydraulic circuit 100 exhibits a dialysis fluid circuit 32 presenting at least one dialysis supply line 8. Depending on the specific apparatus treatment mode, the dialysis supply line 8 may or, may not, assume different hydraulic circuit line configurations. In a hemodialysis (HD) treatment mode, the supply line 8 is destined to transport a dialysis fluid from at least one source 14 towards a treatment station 15 where one or more filtration units 2, or dialyzers, operate. Dialysis fluid and blood exchange through the semipermeable membrane in the filtration unit 15 mainly by diffusion process. In a hemofiltration (HF) treatment mode, the supply line 8 comprises an infusion line 39, which is destined to transport an infusion fluid from at least one source 14 to the blood circuit. The infusion line 39 may include an ultrafilter 44 to additionally filter the received fluid upstream the injection point into the blood circuit. The removal of waste products from the blood is achieved by using large amounts of ultrafiltration with simultaneous reinfusion of sterile replacement fluid in the blood circuit. In a hemodiafiltration (HDF) treatment mode, the supply line 8 is destined to transport the dialysis fluid from the source 14 towards the treatment station 15 and also comprises the infusion line 39 to transport the infusion fluid from the source 14 to the blood circuit 17. HDF is a combination of hemodialysis and hemofiltration. In general, though not essential, the source 14 for the supply line 8 and the infusion line 39 is the same (i.e. a dialysis fluid preparation devices 9).

Of course, different sources may be used. Additionally, the supply line 8 normally branches into the infusion line 39, infusing fluid in the blood circuit 17, and into an inlet line 45 directing the fluid to the treatment station 15. Referring to FIG. 1, a branch point is indicated with reference numeral 46. Notwithstanding the fact that different hydraulic circuits 100 may be used to deliver HF, HD and HDF treatments having exclusively the relevant lines for the specific treatment (e.g. no infusion line 39 for HD, no inlet line 45 for HF), generally the hydraulic circuit 100 is of the kind shown in FIG. 1 and includes both infusion line 39 and inlet line 45, the apparatus control unit 12 may then control the passage of fluid trough said lines, depending on the selected treatment, through e.g. proper valves or clamps. The dialysis fluid circuit 32 further comprises at least one dialysis effluent line 13, destined for the transport of a dialysate liquid (spent dialysate and liquid ultrafiltered from the blood through a semipermeable membrane 5) from the treatment station 15 towards an evacuation zone, schematically denoted by 16 in FIG. 1. The hydraulic circuit cooperates with a blood circuit 17, also schematically represented in FIG. 1 in its basic component parts. The specific structure of the blood circuit is also not fundamental, with reference to the present invention. Thus, with reference to FIG. 1, a brief description of a possible embodiment of a blood circuit is made, which is however provided purely by way of non-limiting example. The blood circuit 17 of FIG. 1 comprises a blood withdrawal line 6 designed to remove blood from a vascular access 18 and a blood return line 7 designed to return the treated blood to the vascular access 18.

The blood circuit 17 of FIG. 1 further comprises a primary chamber 3, or blood chamber, of the blood filtration unit 2, the secondary chamber 4 of which is connected to the hydraulic circuit 100. In greater detail, the blood withdrawal line 6 is connected at the inlet of the primary chamber 3, while the blood return line 7 is connected at the outlet of the primary chamber 3. In turn, the dialysis supply line 8 is connected at the inlet of the secondary chamber 4, while the dialysis effluent line 13 is connected at the outlet of the secondary chamber 4. The filtration unit 2, for example a dialyzer or a plasma filter or a hemofilter or a hemodiafilter, comprises, as mentioned, the two chambers 3 and 4 which are separated by a semipermeable membrane 5, for example of the hollow-fiber type or plate type. The blood circuit 17 may also comprise one or more air separators 19: in the example of FIG. 1 a separator 19 is included at the blood return line 7, upstream of a safety valve 20. Of course other air separators may be present in the blood circuit, such as positioned along the blood withdrawal line 6. The safety valve 20 may be activated to close the blood return line 7 when, for example, for security reasons the blood return to the vascular access 18 has to be halted. The extracorporeal blood treatment apparatus 1 may also comprise one or more blood pumps 21, for example positive displacement pumps such as peristaltic pumps; in the example of FIG. 1, a blood pump 21 is included on the blood withdrawal line 6. The apparatus of above-described embodiment may also comprise a user interface 22 (e.g. a graphic user interface or GUI) and a control unit 12, i.e. a programmed/programmable control unit, connected to the user interface. The control unit 12 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description. In combination with one or more of the above characteristics, the medical apparatus may also comprise a closing device operating, for example, in the blood circuit 17 and/or in the dialysis fluid circuit 32 and commandable between one first operating condition, in which the closing device allows a liquid to flow towards the filtration unit 2, and a second operative position, in which the closing device blocks the passage of liquid towards the filtration unit 2. In this case, the control unit 12 may be connected to the closing device and programmed to drive the closing device to pass from the first to the second operative condition, should an alarm condition have been detected. In FIG. 1 the closing device includes the safety valve 20 (e.g. a solenoid valve) controlled by the unit 12 as described above. Obviously a valve of another nature, either an occlusive pump or a further member configured to selectively prevent and enable fluid passage may be used. Alternatively or additionally to the safety valve 20, the closing device may also comprise a bypass line 23 which connects the dialysis fluid supply line 8 and the dialysate effluent line 13 bypassing the dialyzer, and one or more fluid check members 24 connected to the control unit 12 for selectively opening and closing the bypass line 23. The components (bypass line 23 and fluid check members 24), which may be alternative or additional to the presence of the safety valve 20 are represented by a broken line in FIG. 1. The check members 24 on command of the control unit close the fluid passage towards the treatment zone and connect the source 14 directly with the dialysis effluent line 13 through the bypass line 23. Again with the aim of controlling the fluid passage towards the filtration unit 2, a dialysis fluid pump 25 and a dialysate pump 26 may be included, located respectively on the dialysis fluid supply line 8 and on the dialysate effluent line 13 and also operatively connected to the control unit 12. The apparatus also comprises a dialysis fluid preparation device 9 which may be of any known type, for example including one or more concentrate sources 27, 28 and respective concentrate pumps 29, 30 for the delivery, as well as at least a conductivity sensor 35. Of course other kinds of dialysis fluid preparation devices 9 might be equivalently used, having a single or further concentrate sources and/or a single or more pumps. Since the dialysis apparatus may comprise various liquid sources 14 (for example one or more water sources, one or more concentrate sources 27, 28, one or more sources 33 of disinfectant liquids) connected to the dialysis supply line 8 with respective delivery lines 36, 37 and 38, the apparatus may exhibit, at each delivery line, a respective check member (not all are shown) and, for example, comprising a valve member 31 and 34 and/or an occlusive pump. The preparation device 9 may be any known system configured for on-line preparing dialysis fluid from water and concentrates. The dialysis supply line 8 fluidly connects the preparation device 9 for preparing dialysis fluid to the filtration unit 2 and/or to the blood circuit 17. The preparation device 9 may be, for example, the one described in the U.S. Pat. No. 6,123,847 the content of which is herein incorporated by reference.

As shown, the dialysis supply line 8 connects the preparation device 9 for preparing dialysis fluid to the filtration unit 2 and comprises a main line 40 whose upstream end is intended to be connected to a source 14 of running water. Delivery line/s 36/37 is/are connected to this main line 40, the free end of which delivery line/s is/are intended to be in fluid communication (for example immersed) in a container/s 27, 28 for a concentrated saline solution each containing sodium chloride and/or calcium chloride and/or magnesium chloride and/or potassium chloride. Concentrate pump/s 29, 30 is/are arranged in the delivery line/s 36/37 in order to allow the metered mixing of water and concentrated solution in the main line 40. The concentrate pump/s 29, 30 is/are driven on the basis of the comparison between 1) a target conductivity value for the mixture of liquids formed where the main line 40 joins the delivery line/s 36/37, and 2) the value of the conductivity of this mixture measured with a conductivity sensor 35 arranged in the main line 40 immediately downstream of the junction between the main line 40 and the delivery line/s 36/37. Therefore, as mentioned, the dialysis fluid may contain, for example, ions of sodium, calcium, magnesium, and potassium and the preparation device 9 may be configured to prepare the dialysis fluid on the basis of a comparison between a target conductivity value and an actual conductivity value of the dialysis fluid measured by the conductivity sensor 35 of the device 9. The preparation device 9 comprises regulating means 10, of a known type (i.e. concentrate pump/s 29, 30), which is configured to regulate the concentration of a specific substance, in particular an ionic substance, in the dialysis liquid.

Generally it is advantageous to control the sodium concentration of the dialysis fluid. The dialysis supply line 8 forms an extension of the main line 40 of the preparation device 9 for preparing dialysis fluid. Arranged in this dialysis supply line, in the direction in which the liquid circulates, there are the first flow meter 41 and the dialysis fluid pump 25. The supply line 8 branches (at branch point 46) into the infusion line 39, which, in the example of FIG. 1, is shown directly connected to the blood return line 7, in particular to the air separator 19 (solid line) via post infusion tract 47b. Alternatively, the infusion line 39 may infuse infusion fluid in the blood withdrawal line 6 via pre-infusion tract 47a, in particular downstream the blood pump 21 (dotted line) at pre-infusion point 48. It is also in the scope of the present description an embodiment including an infusion line 39 branching into a pre-infusion branch 47a and in a post infusion branch 47b directing infusion fluid, respectively, in the blood withdrawal line 6 and in the blood return line 7. One or more infusion pumps 43 may be used to pump the desired flow of infusion fluid into the blood circuit. The infusion pump 43 may be a positive displacement pump (e.g. a peristaltic pump as shown) or any other pump configured to displace infusion fluid (e.g. a volumetric pump). The dialysis effluent line 13 may be provided with a dialysate pump 26 and a second flow meter 42. The first and second flow meters 41, 42 may be used to control (in a known manner) the fluid balance of a patient connected to the blood circuit 17 during a dialysis session.

A sensor 11 is provided on the dialysis effluent line 13, immediately downstream the filtration unit 2, to measure a parameter value of the dialysate in the dialysate effluent line. In detail, the parameter of the dialysate, which is measured by the sensor 11 is at least one chosen in the group consisting of conductivity of the dialysate, a conductivity-related parameter of the dialysate, concentration of at least a substance in the dialysate and a concentration-related parameter of at least a substance in the dialysate. In detail the sensor 11 is a conductivity sensor, which is connected to the dialysis effluent line 13, and is configured to detect conductivity values of the dialysate downstream of the filtration unit 2. Alternatively (or in combination) sensor 11 may include a concentration sensor configured for measuring the concentration of at least one substance in the dialysate, such as sodium concentration. Correspondingly, sensor 35 on the dialysis fluid supply line may be not a conductivity sensor and, differently, may include a concentration sensor configured for measuring the concentration of at least one substance in the dialysis fluid, such as sodium concentration. The control unit 12 of the dialysis apparatus represented in FIG. 1 may be connected to a (graphic) user interface 22 through which it may receive instructions, for example target values, such as blood flow rate $Q_b$, dialysis fluid flow rate $Q_{di}$, infusion liquid flow rate $Q_{inf}$ (pre infusion and/or post infusion), patient weight loss WL. The control unit 12 furthermore may receive detected values by the sensors of the apparatus, such as the aforementioned flow meters 41, 42, the (e.g. conductivity) sensor 35 of the preparation device 9 and the (e.g. conductivity) sensor 11 in the dialysis effluent line 13. On the basis of the instructions received and the operating modes and algorithms which have been programmed, the control unit 12 drives the actuators of the apparatus, such as the blood pump 21, the aforementioned dialysis fluid and dialysate pumps 25, 26, and the preparation device 9, and the infusion pump 43. As already mentioned, the described embodiments are intended to be non-limiting examples. In particular the circuits of FIG. 1 should not be interpreted as defining or limiting, as an apparatus such as in the invention may comprise other additional or alternative components to those described. For example an ultrafiltration line may be included, with at least one respective pump connected to the dialysis effluent line 13. The blood circuit of FIG. 1 is intended for double needle treatments; however, this is a non-limiting example of the blood set. Indeed, the apparatus may be configured to perform single needle treatments, i.e. the patient is connected to the extracorporeal blood circuit by way of a single needle and the extracorporeal line from the patient is then split into a withdrawal line and a return line, using, for example, a 'Y' connector. During single needle treatment, a blood withdrawal phase removing blood from patient is alternated to a blood return phase in which blood is restituted to the patient. Furthermore one or more devices for measuring specific substance concentrations might be implemented either (or both) in the dialysis fluid side or (and) in the blood side of the hydraulic circuit. Concentration of calcium, potassium, magnesium, bicarbonate, and/or sodium might be desired to be known. Finally, the above-cited one or more pumps and all the other temperature, pressure, and concentration sensors may operate either on the dialysis supply line 8 and/or on the dialysis effluent line 13, in order to adequately monitor the preparation and movement of the liquid in the hydraulic circuit. Given the above description of a possible embodiment of extracorporeal blood treatment apparatus, thereafter the specific working of the apparatus and the algorithm programming the control unit are described.

Definitions

We define the "dialysis fluid" as the fluid prepared and, when appropriate based on the selected treatment, introduced to the second chamber (4) of the filtration unit (2)—e.g. HD and HDF the dialyzer. The dialysis fluid may also be denoted "fresh dialysis fluid".

We define the "dialysate" as the fluid from the outlet from the second chamber (4) of the filtration unit (2), the dialyzer. Dialysate is the spent dialysis fluid, comprising the uremic toxins removed from the blood.

We define "infusion fluid" as the fluid prepared and infused in the blood circuit (17), either in the blood withdrawal line (6) or in the blood return line (7) or in both blood lines (6, 7).

We define 'isonatric dialysis' as a treatment where the sodium concentration of the dialysis fluid does not change pre- to post-filtration unit 2. It is then assumed that the sodium concentration of the dialysis fluid matches the sodium concentration of the plasma, and thus the diffusive sodium mass transfer is zero.

We define 'isotonic dialysis', as a treatment where the tonicity of the dialysis fluid does not change pre- to post-filtration unit 2. It is then assumed that the tonicity of the dialysis fluid matches the tonicity of the plasma.

We define 'plasma conductivity' (PC, $k_p$) as the conductivity of the dialysis fluid in an isoconductive dialysis.

We define 'hemodialysis treatment mode' (HD) a dialysis treatment with fresh dialysis fluid is directed to the filtration unit 2 and no substitution fluid is infused in the blood circuit.

We define 'hemofiltration treatment mode' (HF) a treatment with substitution fluid directed into the blood circuit 17 and no fresh dialysis fluid is directed to the filtration unit 2.

We define 'hemodiafiltration treatment mode' (HDF) a treatment with both substitution fluid directed into the blood circuit 17 and fresh dialysis fluid directed to the filtration unit 2.

We define the 'total ultrafiltration flow' $Q_u$ as the sum of the weight loss flow rate $Q_{wl}$, and the infusion flow $Q_{inf}$;

$$Q_u = Q_{wl} + Q_{inf}$$

In HD treatment mode, the infusion flow $Q_{inf}$ is zero.

We define the 'dialyzer inlet fluid flow' as:

$$Q_{di} = Q_d - Q_{inf}$$

where $Q_d$ is the total dialysis fluid flow rate, i.e. the total flow rate of dialysis fluid which is prepared by the preparation device 9 and which is then split (if appropriate) into a fluid flow ($Q_{di}$) to the filtration unit and a fluid flow ($Q_{inf}$) to be infused in the blood circuit. We define the 'dialyzer outlet fluid flow' $Q_{do}$ as:

$$Q_{do} = Q_{di} + Q_u$$

Glossary

The following terms are consistently used throughout the equations provided in the following description of the detailed working of the extracorporeal blood treatment apparatus.

| Name | Description | Unit |
|---|---|---|
| $\kappa_{di}$ | Dialysis fluid conductivity upstream the filtration unit; | mS/cm |
| $\kappa_{do}$ | Dialysate conductivity downstream the filtration unit; | mS/cm |
| $\kappa_p$ | Plasma conductivity; | mS/cm |
| $c_{di}$ | Concentration of at least a substance in the dialysis fluid at the inlet of the filtration unit; | mmol/L |
| $c_{do}$ | Concentration of at least a substance in the dialysate at the outlet of the filtration unit; | mmol/L |
| $c_{bi}$ | Concentration of at least a substance in the blood at the inlet of the filtration unit; | mmol/L |
| $Q_{di}$ | Dialysis fluid flow rate at filtration unit inlet; | mL/min |
| $Q_d$ | Total dialysis fluid flow rate; | mL/min |
| $Q_{inf}$ | Dialysis fluid infusion flow rate, e.g. dialysis fluid directly infused in the blood circuit; | mL/min |
| $Q_{do}$ | Dialysate flow rate at filtration unit outlet (i.e., $Q_{di} + Q_{uf}$); | mL/min |
| $Q_{wl}$ | Weight loss rate; | mL/min |
| $Q_{uf}$ | Ultrafiltration flow rate; | mL/min |
| $Q_{bset}$ | Set blood flow rate at filtration unit inlet; | mL/min |
| $Q_b$ | Real blood flow rate at filtration unit inlet; | mL/min |
| $K_u$ | Filtration unit clearance for urea; | mL/min |
| $k_{p,1}$ and $k_{p,2}$ | 1st and 2nd estimate of plasma conductivity; | mS/cm |
| D | Ionic dialysance | mL/min |
| $\Delta$ | Gradient | mS/cm |
| T | Set total treatment time; | min |
| t | Elapsed time into treatment; | min |

Solution Proposal

The technical solution here described is applicable to HD and HDF treatment modes, particularly making use of concentrates to prepare the fresh dialysis fluid. The solution consists of the following main aspects:

Setting the dialysis fluid sodium concentration/conductivity at an initial set point value according to the physician prescription;

Assuming the initial set point value for the dialysis fluid to be the target plasma conductivity/plasma sodium concentration which the patient blood has to reach, or has to tend to, at the end of the dialysis treatment (i.e. the target plasma conductivity/sodium concentration is equivalent to the dialysate conductivity/sodium concentration prescribed);

Estimating plasma conductivity (i.e., $k_p$) at the beginning of the treatment; in more detail, isoconductivity is estimated at the beginning of treatment. In particular, the estimation is done either:

with an iterative method: after one/two iterations the estimated value is generally considered sufficiently accurate; or imposing a step in the fresh dialysis conductivity/concentration and measuring the response in the spent dialysate (Diascan® measurement);

Calculating a constant gradient between the dialysis fluid sodium concentration/conductivity in the dialysis supply line and the plasma conductivity/the plasma sodium concentration that allows to reach the target final plasma conductivity/plasma sodium concentration;

Setting the dialysis fluid sodium concentration/conductivity at the updated value calculated for sodium concentration/conductivity in the dialysis supply line;

Updating plasma conductivity value/ionic dialysance during the treatment and calculating new updated values for the dialysis fluid sodium concentration/conductivity using the already calculated constant gradient.

The various steps of the proposed method described below are intended to be performed by the control unit 12 of the extracorporeal blood treatment device 1, even if not explicitly stated. A treatment session is started, optionally, but not necessarily, as a double needle hemodialysis treatment. The user shall input the treatment mode (e.g. HD or HDF) and the prescription values through the user interface 22. For example the set values for total weight loss WL and total treatment time T are provided, as well as the blood flow rate $Q_b$ and the fresh dialysis flow rate $Q_d$. The dialysis fluid composition is also provided, including its initial sodium concentration. If required also infusion rate $Q_{inf}$ or the total accumulated infusion volume ($V_{inf}$), is provided. Other parameters may be entered through the user interface, such as concentrate type, sodium user limits, etc. The operator may further input the 'bicarbonate' set before starting the treatment. The control unit 12 set either the initial dialysis liquid conductivity or the initial concentration of at least one solute, e.g. sodium, in the dialysis liquid based on the prescription in order to start the treatment. In this respect it is worth to note that, in the following detailed description, reference is made to regulating means controlling concentration of an ionic substance, in detail sodium concentration, in the preparation of the dialysis fluid so as to obtain a desired conductivity of the dialysis fluid.

However, regulating means directly regulating the overall dialysis fluid conductivity is also included in the spirit of the present description or, alternatively, regulating means modifying the concentration of a different ionic substance is included in the present description, too.

Given the above, the control unit 12 sets the parameter value for the dialysis fluid in the dialysis fluid supply line 8 at an initial set point; in general the parameter of the dialysis fluid is either the conductivity of the dialysis fluid, or a conductivity-related parameter of the dialysis fluid, or concentration of at least a substance (in particular a ionic substance and in more detail sodium) in the dialysis fluid, or a concentration-related parameter of at least a substance (e.g. sodium) in the dialysis fluid. Depending on the specific dialysis monitor, the sodium content (or the content of more than one electrolyte) may be regulated in the dialysis line. Alternatively, the control parameter may be the overall conductivity of the dialysis fluid. In the specific, the control unit 12 receives the initial set point of sodium concentration and drives the regulating means 10 acting on the sodium concentration in the dialysis liquid. The initial set point is imposed before starting the blood circulation (i.e. before starting the treatment).

Once the sodium initial set point has been set and a corresponding dialysis fluid has been prepared by the control unit 12 driving the regulating means 10, the treatment may start. The dialysis fluid is prepared and then circulated through the dialysis fluid circuit 32.

Correspondingly, blood is withdrawn from the patient and circulated in the extracorporeal blood circuit 17 and particularly is circulated through the primary chamber 3 of the filtration unit 2. The control unit 12 determines the value of a parameter relating to the efficiency of the filtration unit 2; in more detail, the control unit 12 has knowledge of the clearance or the ionic dialysance D of the filtration unit 2. The ionic dialysance may be received e.g., as input from a user or from a memory of a database, may be measured e.g., lab test, or calculated e.g., as described in patents EP 547025 or EP 920877 (e.g. Diascan® measure). Furthermore, the control unit 12 determines the plasma conductivity (or the plasma concentration of at least a substance, namely sodium, in the blood—herein after reference is made to plasma conductivity mainly, without the invention being limited to this blood parameter) of the specific patient.

In particular, the control unit 12 may be programmed for calculating the plasma conductivity, for example executing the method disclosed in the following paragraphs ("First estimation of plasma conductivity") or, alternatively using known methods—e.g., the Diascan® method from the applicant—such as the methods described in EP 2377563, EP 547025 or EP 920877. Alternatively, the control unit 12 directly receives as an input the plasma conductivity. For example, the physician or the nurse may receive a lab analysis and may provide the datum to the machine through the user interface of the dialysis monitor; the control unit 12 is programmed for storing in a memory the plasma conductivity to be used for the following dialysis fluid parameter regulation. Finally, the plasma conductivity may be directly measured in vivo by the monitor before starting the treatment session using a proper plasma conductivity sensor. Additionally, the control unit 12 receives values of the parameter of the dialysate, namely conductivity values, measured downstream of said secondary chamber 4. The solution for determining and adjusting the sodium concentration/conductivity in the fresh dialysis fluid includes calculating the updated value of the parameter for the dialysis fluid in the dialysis supply line 8 based on the measured parameter value (conductivity/concentration) of the dialysate in the dialysis effluent line 13, the parameter relating to the efficiency of the filtration unit 2 (ionic dialysance) and a gradient between the current value of the parameter value (conductivity/concentration) for the dialysis fluid in the dialysis supply line 8 and the plasma conductivity or the sodium plasma concentration of in the blood. In more detail, the gradient is defined as follows:

$$\Delta = (c_{di} - c_{bi})$$

or $$\Delta = (\kappa_{di} - \kappa_{bi}) \quad (I)$$

wherein $c_{di}$ is the concentration of sodium in the dialysis fluid at the inlet of the filtration unit;

$c_{bi}$ is the concentration of sodium in the blood;

$\kappa_{di}$ is the conductivity of the dialysis fluid at the inlet of the filtration unit;

$\kappa_{bi}$ is the plasma conductivity.

The gradient is therefore defined either by a difference between dialysis fluid and plasma conductivities or by a difference in sodium concentrations between dialysis fluid and blood.

In more detail, the control unit is configured to calculate the updated value of the conductivity or sodium concentration for the dialysis fluid in the dialysis supply line 8 based on one of the following formulas:

$$c_{di} = c_{do} + \frac{\Delta \cdot D}{Q_d + Q_{wl}} \quad (II)$$

or $$\kappa_{di} = \kappa_{do} + \frac{\Delta \cdot D}{Q_d + Q_{wl}}$$

wherein $c_{di}$ is the concentration of at least a substance in the dialysis fluid at the inlet of the filtration unit;

$c_{do}$ is the concentration of at least a substance in the dialysate at the outlet of the filtration unit;

$\kappa_{di}$ is the conductivity of the dialysis fluid at the inlet of the filtration unit;

$\kappa_{do}$ is the conductivity of the dialysate at the outlet of the filtration unit;

$\Delta$ is the gradient;

D is the parameter relating to the efficiency of the filtration unit 2;

$Q_d$ is the dialysate flow rate;

$Q_{wl}$ is the weight loss rate.

The above formula might be applied for both HD and HDF treatments.

With respect to all the above sodium concentrations/conductivities set for dialysis treatments, it is worth to note that the calculated and proposed concentration shall be within the sodium set user limits.

These limits may be chosen by the operator before the dialysis start, within the following limits:

For instance, the absolute safety range (e.g. 120÷160 mmol/l);

the sodium range corresponding to the conductivity allowed range of the machine (e.g. 12÷16 mS/cm), given the used bag and the prescribed bicarbonate.

Generally, if the calculated sodium concentration value for the set falls outside the user range, the control should be de-activated and/or at least a warning is given to the operator.

Figure 2:
FIG. 2 is a schematic representing an isotonic dialysis treatment with conductivity (or sodium concentration) gradient equal to 0.

The above formula (II) allows to realize a flexible and simple biofeedback system that permits to perform both isotonic dialysis or dialysis with positive/negative sodium gradients, avoiding changes in prescription parameters and continuing to work with safe clinical conditions regardless of the type of treatment chosen. The system is be based on the concept of sodium concentration (or conductivity) gradient A. Since the gradient is defined as in formula (I), e.g. $\Delta=(c_{di}-c_{bi})$, i.e. as the conductivity gradient between dialysate and plasma, hence, prescribing $\Delta=0$ it is possible to perform an isotonic treatment (see FIG. 2).

Figure 3:
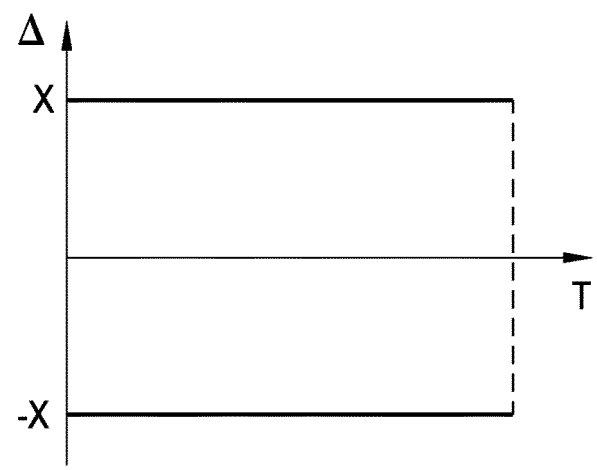
FIG. 3 is a schematic showing non-isotonic dialysis treatment with conductivity (or sodium concentration) gradient different from 0.

Setting a positive or negative A (see FIG. 3), it is possible to change the total sodium mass of the patient, basing on his/her clinical needs, maintaining a constant gradient through the entire session. The system may automatically and continuously adjust $c_{di}$, according to Eq (II), in order to track the desired A trajectory. Since the plasma conductivity/plasma sodium concentration varies during the treatment, due to the imposed gradient, the updated plasma conductivity/plasma sodium concentration after an elapsed treatment time t is to be updated. Again the updated value may be received by the control unit, for example from a lab analysis or from a sensor measuring plasma conductivity.

In general, the updated value for the plasma conductivity/plasma sodium concentration is determined according to the Diascan® procedure, for example in accordance with any of the methods described in EP 2377563, EP 547025 or EP 920877. In addition, the calculation procedure also provides a new estimate for the efficiency parameter for the filtration unit, namely of the ionic dialysance. The updated values for these two parameters are then used in the formula to determine the updated value for the conductivity (or sodium concentration) of the dialysis fluid. Since in calculating the updated value for the conductivity (or sodium concentration) of the dialysis fluid the gradient is kept constant, the above formula (II) allows to easily re-determine the updated set point for the dialysis fluid. In other terms, the physician does not need to prescribe the gradient value in case of non-isotonic dialysis: this value is automatically determined by the machine, starting from the initial patient plasma conductivity, estimated e.g. at the first Diascan® measure, and is based only on the target plasma conductivity/sodium concentration in blood, which is equivalent to the dialysate conductivity/sodium concentration as prescribed.

Figure 4:
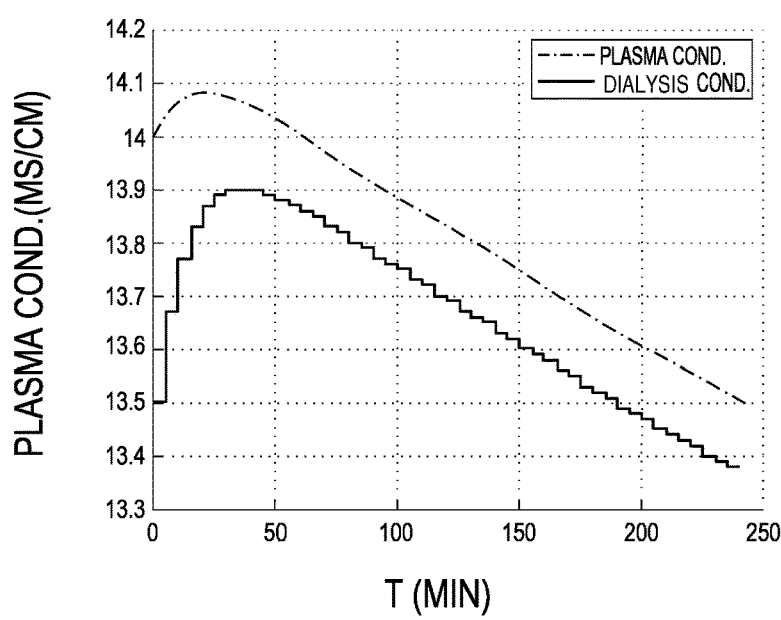
FIG. 4 is a diagram showing an example of treatment executed with a constant gradient between plasma conductivity (in red) and dialysate conductivity (in blue); the final target of the patient is achieved maintaining the constant gradient value estimated by the model at first blood sodium concentration and dialysance measures.

Hence, the required prescription parameters remain unchanged with respect to conventional hemodialysis treatments: dialysate and blood flows, treatment time, weight loss, distribution volume and dialysate composition. In particular, the dialysate conductivity/sodium concentration prescribed represents, as in a conventional treatment, the final target that shall be achieved for the patient. For example, at the first Diascan measure, the system estimates the initial plasma conductivity/sodium concentration of the patient: this is the input for a double-pool sodium kinetic model implemented into the machine. The model runs iteratively and finds the constant gradient A that allows to reach the prescribed final plasma conductivity/sodium concentration. Once the A value has been calculated, the system automatically and continuously regulates the $c_{di}$ (or $\kappa_{di}$) set point, according to Eq. (II), in order to maintain the constant gradient determined by the model for all the treatment (see FIG. 4). FIG. 4 is an example of treatment executed with a constant gradient between plasma conductivity and dialysate conductivity. The final target of the patient is achieved maintaining the constant gradient value estimated by the model at first Diascan® measure. In detail, the prescribed dialysis fluid conductivity (13.5 mS/cm) becomes the final target for the patient plasma conductivity. The gradient A (estimated by the model) is in this case 0.16 mS/cm. As can be clearly seen, the dialysis fluid conductivity is not varied continuously, but step by step. Of course time variation and height of each step may be eventually configured.

First Estimation of Plasma Conductivity (Estimation of Isoconductivity)

As mentioned, the initial plasma conductivity may be differently (or additionally) estimated as follows. The control unit 12 is configured to impose the initial set point of the substance concentration to be set (e.g. sodium) in the dialysis fluid based on the prescription. Once the sodium initial set point has been set and a corresponding dialysis fluid has been prepared by the control unit 12 driving the regulating means 10, the treatment starts.

Depending on the selected treatment mode, the dialysis fluid is directed:
- to the secondary chamber 4 of the filtration unit 2 only so as to exchange with blood (HD mode);
- to the secondary chamber 4 of the filtration unit 2 so as to exchange with blood and infused into the blood circuit 17 (HDF mode);
- to the blood circuit only (HF mode); in this case an ultrafiltration flow rate is set to achieve a $Q_u = Q_{do}$.

Correspondingly, blood is withdrawn from the patient and circulated in the extracorporeal blood circuit 17. At least one, and in general a plurality, of consecutive initial values of the parameter (in the specific example, the conductivity) of the dialysate downstream of the secondary chamber 4 are measured at the beginning of the treatment through sensor 11. The post-dialyzer conductivity will change initially, due to e.g. dynamics when treatment is started (e.g. leaving bypass conditions) or when blood flow is ramped up. However, it is expected to stabilize within few (e.g. 4) minutes. As mentioned, a transient exists when dialysis fluid and blood start exchanging during which the dialyzer outlet conductivity is not stable; during the transient period the measured outlet conductivity values should be disregarded. In order to minimize the time needed to reach stability conditions, changes in dialysis fluid flow rate and in bicarbonate prescription may be prevented; changes in blood flow, ultrafiltration flow rate or bypass are vice versa generally allowed, but they will delay stability. It is relevant to measure at least the conductivity downstream the filtration unit (and possibly also the conductivity upstream the filtration unit) as soon as possible, i.e. as soon as stable conditions are reached or as soon as an estimate of such conductivity in stable conditions may be performed. This is due to the need of precisely estimate the patient initial plasma conductivity which is affected/changed by the different conductivity of the dialysis fluid circulating during the treatment. In order to make a first estimate of the plasma conductivity based on measured values, two embodiments are provided, which may be used together or alternatively.

Firstly, the control unit 12 calculates the value of the initial plasma conductivity, based on the measured initial parameter value of the dialysate (i.e. based on conductivity or concentration measurement of dialysate on the filtration unit outlet) and on the corresponding parameter value of the dialysis fluid in the dialysis fluid supply line 8 e.g. conductivity or concentration. During the start of the treatment and particularly during circulating the dialysis fluid through the secondary chamber 4 and/or in the infusion line 39 up to measuring the initial value of the parameter of the dialysate downstream of the secondary chamber used for the calculating of the initial plasma conductivity, the dialysis fluid conductivity (or concentration) is kept substantially constant. In other words, in this specific example, the calculation of the initial plasma conductivity is performed with no conductivity step. Indeed, both the two embodiments allowing plasma conductivity estimation do not require to change the dialysis conductivity or the sodium content in the dialysis liquid and to take measures at the inlet and at the outlet of the dialyzer in both conditions. In this respect the term 'substantially constant' means that the conductivity of the dialysis fluid is not changed by the machine or by the operator, but it may not be exactly constant due to small oscillations on the measured value caused by noise, tolerances in the concentrate dosing system or tolerances in the conductivity measurements. Generally these small variations around the set value are less than 0.2 mS/cm.

Just a single reliable measurement at the inlet and at the outlet of the dialyzer may be sufficient to have a preliminary (to be made more accurate) or an already final estimation of the plasma conductivity. From a general point of view, the control unit 12 is further configured to calculate the plasma conductivity as a function of at least one or more flow rates, including the dialysate flow rate at the outlet of the secondary chamber 4; in addition, the flow rates may include the blood flow rate in the blood lines too. Also an efficiency parameter of the filtration unit 2, in particular a clearance of the filtration unit 2 (e.g. the urea clearance) is used for plasma conductivity. Of course, a nominal clearance and/or a calculated clearance may be used; the calculated clearance may be both an estimated clearance as well as a compensated clearance. Moreover, the plasma conductivity depends on an initial conductivity of the dialysate and on a conductivity of the dialysis fluid in the dialysis supply line 8. According to a first embodiment, the control unit 12 is programmed to calculate the initial plasma conductivity based on the sum of at least the initial conductivity of the dialysate plus a difference between inlet and outlet conductivity at the filtration unit, or dialyzer, weighted by a factor of the dialysate flow rate. In more detail the difference between inlet and outlet conductivity at the dialyzer is weighted by a factor of the blood flow rate in the blood lines too.

Specifically, according to the first embodiment, the control unit 12 is configured to calculate the plasma conductivity using the following formula:

$$\kappa_p = \kappa_{do} + \frac{Q_{do}}{Q_{bset}}(\kappa_{do} - \kappa_{di}) \qquad (III)$$

The significance of the denotations above is given in the Glossary.

It is worth to underline that during the above described calculation of the initial plasma conductivity (formula (III)), the dialysis fluid circulates through the secondary chamber 4 and/or is infused into the blood circuit 17 (depending on selected HD/HF/HDF mode) maintaining the dialysis fluid parameter value substantially constant.

In the second embodiment, the control unit 12 is programmed to calculate the initial plasma conductivity based on the sum of at least the initial conductivity of the fresh dialysis fluid plus a difference between inlet and outlet conductivity at the dialyzer weighted by a factor of the dialysate flow rate. In more detail the difference between inlet and outlet conductivity at the filtration unit, or dialyzer, is weighted by a factor of the dialyzer clearance too. Specifically, according to the second embodiment, the control unit 12 is configured to calculate the plasma conductivity using the following formula:

$$\kappa_p = \kappa_{do} + \frac{Q_{do}}{K_u}(\kappa_{do} - \kappa_{di}) \qquad (IV)$$

The significance of the denotations and constants above is given in the Glossary.

It is worth to underline that during the above described calculation of the initial plasma conductivity (formula (IV)), the dialysis fluid circulates through the secondary chamber 4 and/or is infused into the blood circuit 17 (depending on selected HD/HF/HDF mode) maintaining the dialysis fluid parameter value substantially constant. In more detail, in the formulas above $K_u$ is the dialyzer diffusive clearance for urea. Since the filtration unit (dialyzer) clearance $K_u$ isn't known, it may be estimated. For the purpose of the estimation, it is assumed that all ions have the same dialyzer clearance, which is equal to the urea clearance. In HDF treatments it is relevant to distinguish between the dialyzer clearance, which is related to the transport across the membrane, and the treatment (patient) clearance which describes the removal of a substance from the patient. The patient clearance has clinical interest, whereas for the purpose of calculating the initial set point the interest is in the dialyzer properties. Thus, when clearance is referred to in this document, unless otherwise stated, it is the filtration unit/dialyzer clearance. The clearance $K_u$ may be calculated as described in PCT publication n. WO2016188950. According to first estimate, $k_p$ may be found after approx. 6 to 10 minutes after treatment start.

Of course, both formulas (III) and (IV) for estimation of plasma conductivity may be iteratively applied, meaning that the newly calculated estimate of plasma conductivity $k_{p,1}$ is imposed to the dialysis fluid and a new estimate $k_{p,2}$ again calculated after taking measures of the conductivity at the inlet and outlet of the filter as soon as stable conditions are reached. Of course, in case of iteration of anyone of the above calculations according to formulas (III) or (IV), after the first plasma conductivity estimation, the dialysis fluid parameter value is changed since the newly calculated estimate of plasma conductivity $k_{p,1}$ is imposed to the dialysis fluid, meaning that the conductivity of the dialysis fluid is changed. This however does not impact on the fact that the first calculation according to formulas (III) and (IV) is made without a change in the conductivity of the dialysis fluid.

In one way of exploiting the method, the first formula (III) or the second formula (IV) is applied only once and the estimated plasma conductivity $k_{p,1}$ is considered already a good estimation of initial plasma conductivity. In another way, the first formula (III) is applied twice.

In a further way, the second formula (IV) is applied twice; in this case, the dialysis fluid sodium concentration correspondent to $k_p$ is iteratively calculated and applied. $k_{do}$ is measured again as soon as stable conditions are reached: the stability criteria are the same as previously described. A second estimation of plasma conductivity $k_{p,2}$ according to formula (IV) is done and $k_{p,2}$ is used as $k_p$.

The proposed solution allows to perform the isotonic dialysis treatment in biofeedback mode with "one button" only. Additionally, it allows to perform non-isotonic dialysis treatment in biofeedback mode with the same set of prescription parameters used in the clinical routine. A desired target of final plasma conductivity/sodium concentration is achieved with a simplified biofeedback control and dialysis with the minimum constant conductivity/concentration gradient between plasma and dialysis fluid is a solution to prevent electrolytic imbalance in patients not treated with isotonic dialysis. While the invention has been described in connection with what is presently considered to be the most practical and preferred embodiment, it is to be understood that the invention is not to be limited to the disclosed embodiment, but on the contrary, is intended to cover various modifications and equivalent arrangements included within the scope of the appended claims.

The invention claimed is:
1. An apparatus for extracorporeal blood treatment comprising:
    a filtration unit having a primary chamber and a secondary chamber separated by a semi-permeable membrane;
    a blood circuit including a blood withdrawal line connected to an inlet of the primary chamber and a blood return line connected to an outlet of the primary chamber, said blood lines being configured for connection to a patient cardiovascular system;
    a dialysis supply line connected to an inlet of the secondary chamber;
    a dialysis effluent line connected to an outlet of the secondary chamber;
    a preparation device configured to prepare a dialysis fluid, the preparation device connected to said dialysis supply line and including a regulator configured to regulate a composition of the dialysis fluid;
    a sensor configured to measure a parameter value of a dialysate in the dialysis effluent line, said parameter value of the dialysate being at least one selected from the group consisting of a conductivity of the dialysate and a concentration of at least a substance in the dialysate; and
    a control unit in communication with the regulator and the sensor, the control unit configured to:
        set a parameter value for the dialysis fluid in the dialysis supply line at an initial set point, said parameter of the dialysis fluid being at least one selected from the group consisting of a conductivity of the dialysis fluid and a concentration of at least a substance in the dialysis fluid;
        circulate, after setting the dialysis fluid parameter value at the initial set point, the dialysis fluid through the secondary chamber of the filtration unit;
        circulate blood through the primary chamber of the filtration unit;
        receive from the sensor measurement values of said parameter of the dialysate downstream of said secondary chamber;
        determine, by receiving, measuring or calculating, a filtration unit parameter relating to an efficiency of the filtration unit;
        determine, by receiving, measuring or calculating, a plasma conductivity or a plasma concentration of at least a substance in the blood;
        calculate an updated value of the parameter for the dialysis fluid in the dialysis supply line based on the parameter value of the dialysate in the dialysis effluent line, the filtration unit parameter relating to the efficiency of the filtration unit and a gradient between a current value of the parameter value for the dialysis fluid in the dialysis supply line and the plasma conductivity or the plasma concentration of at least a substance in the blood; and
        command the regulator for regulating the composition of the dialysis fluid in the dialysis supply line at the updated value,
        wherein calculating the updated value includes keeping the gradient substantially constant.
2. The apparatus of claim 1, wherein said at least a substance in the blood is sodium.
3. The apparatus of claim 1, wherein the control unit is configured to calculate the updated value of the parameter for the dialysis fluid in the dialysis supply line based on a dialysis flow rate and on a weight loss rate through the filtration unit.

4. The apparatus of claim 1, wherein the control unit is configured to calculate the updated value of the parameter for the dialysis fluid in the dialysis supply line based on a sum of a dialysis flow rate and a weight loss rate through the filtration unit.

5. The apparatus of claim 1, wherein the gradient is defined as:

$$\Delta = (c_{di} - c_{bi})$$

or $$\Delta = (\kappa_{di} - \kappa_{bi})$$

wherein, $c_{di}$ s the concentration of at least a substance in the dialysis fluid at an inlet of the filtration unit, $c_{bi}$ is a concentration of at least a substance in the blood, $\kappa_{di}$ is the conductivity of the dialysis fluid at the inlet of the filtration unit, and $\kappa_{bi}$ is the plasma conductivity, wherein the gradient is defined either by a difference between conductivities or by a difference in concentrations of a substance.

6. The apparatus of claim 1, wherein said substance in the blood, said substance in the dialysis fluid in the dialysis supply line, and said substance in the dialysate in the dialysis effluent line are each sodium.

7. The apparatus of claim 1, wherein the filtration unit parameter relating to the efficiency of the filtration unit is a clearance or a dialysance of the filtration unit.

8. The apparatus of claim 1, wherein the control unit is configured to calculate the updated value of the parameter for the dialysis fluid in the dialysis supply line based on a sum of a first term and a second term, the first term including the parameter value of the dialysate in the dialysis effluent line and the second term including the filtration unit parameter relating to the efficiency of the filtration unit and the gradient.

9. The apparatus of claim 8, wherein the second term includes one or more of a dialysate flow rate, a weight loss rate through the filtration unit, an infusion flow rate, an ultrafiltration flow rate, or a dialysate flow rate at filtration unit outlet.

10. The apparatus of claim 8, wherein the first term is the parameter value of the dialysate in the dialysis effluent line, and wherein the second term is proportional to both the filtration unit parameter relating to the efficiency of the filtration unit and the gradient.

11. The apparatus of claim 8, wherein the second term is inversely proportional to at least one of a dialysate flow rate at an inlet of the filtration unit, an ultrafiltration flow rate through the filtration unit, and a dialysate flow rate at an outlet of the filtration unit.

12. The apparatus of claim 8, wherein the second term is inversely proportional to either a dialysate flow rate at an outlet of the filtration unit or to the sum of the dialysate flow rate at an inlet of the filtration unit and an ultrafiltration flow rate through the filtration unit.

13. The apparatus of claim 1, wherein the control unit is configured to calculate the updated value of the parameter for the dialysis fluid in the dialysis supply line based on one of the following formulas:

$$c_{di} = c_{do} + \frac{\Delta \cdot D}{Q_d + Q_{wl}}$$

or $$\kappa_{di} = \kappa_{do} + \frac{\Delta \cdot D}{Q_d + Q_{wl}}$$

wherein, $c_{di}$ is the concentration of at least a substance in the dialysis fluid at an inlet of the filtration unit, $c_{do}$ is the concentration of at least a substance in the dialysate at an outlet of the filtration unit, $\kappa_{di}$ is the conductivity of the dialysis fluid at the inlet of the filtration unit, $\kappa_{do}$ is the conductivity of the dialysate at the outlet of the filtration unit, $\Delta$ is the gradient, D is the filtration unit parameter relating to the efficiency of the filtration unit, $Q_d$ is a dialysate flow rate, and $Q_{wl}$ is a weight loss rate.

14. The apparatus of claim 1, wherein the control unit is configured to receive as an input the initial set point of the parameter value for the dialysis fluid in the dialysis supply line, and wherein the control unit is configured to determine the gradient such that a value of the plasma conductivity or of the plasma concentration of at least a substance in the blood is achieved at an end of the extracorporeal blood treatment that tends to, or coincides with, the initial set point of the parameter value.

15. The apparatus of claim 1, wherein the control unit is configured to receive as an input a desired value of the plasma conductivity or of the plasma concentration of at least a substance in the blood to be reached at an end of the extracorporeal blood treatment, and wherein the control unit is configured to determine the gradient such that the desired value of the plasma conductivity or the plasma concentration of at least a substance in the blood is achieved at the end of the extracorporeal blood treatment.

16. The apparatus of claim 1, wherein the control unit is configured to calculate the plasma conductivity according to the following formula:

$$\kappa_p = \kappa_{do} + \frac{Q_{do}}{Q_{bset}}(\kappa_{do} - \kappa_{di})$$

wherein:

$\kappa_P$ is the plasma conductivity, $Q_{do}$ is a dialysate flow rate at an outlet of the filtration unit, $Q_{bset}$ is a set blood flow rate at an inlet of the filtration unit, $k_{di}$ is the dialysis fluid conductivity at the inlet of the filtration unit, and $k_{do}$ is the dialysate conductivity at the outlet of the filtration unit, or according to the following formula:

$$\kappa_p = \kappa_{do} + \frac{Q_{do}}{K_u}(\kappa_{do} - \kappa_{di})$$

wherein:

$\kappa_P$ is the plasma conductivity, $Q_{do}$ is a dialysate flow rate at the outlet of the filtration unit, $K_u$ is a filtration unit clearance for urea, $k_{di}$ is the dialysis fluid conductivity at the inlet of the filtration unit, and $k_{do}$ is the dialysate conductivity at the outlet of the filtration unit.

17. The apparatus of claim 1, wherein the control unit is configured to calculate the plasma conductivity or the plasma concentration, and the filtration unit parameter relating to the efficiency of the filtration unit, from at least two parameter values of the dialysis fluid and of the dialysate determined respectively upstream and downstream of said filtration unit in at least two successively prepared dialysis fluids with different concentrations of a substance, said control unit configured to perform said calculation a plurality of times and at predetermined times during the extracorporeal blood treatment.

18. The apparatus of claim 1, wherein the control unit is configured to determine the plasma conductivity or the plasma concentration of at least a substance in the blood a plurality of times during the extracorporeal blood treatment, a respective updated value of the parameter for the dialysis fluid in the dialysis supply line being calculated each time when the plasma conductivity or the plasma concentration is newly determined during the extracorporeal blood treatment, wherein calculating the respective updated value includes keeping the gradient substantially constant.

19. The apparatus of claim 1, wherein the control unit is configured to determine the filtration unit parameter relating to the efficiency of the filtration unit, the updated value of the parameter for the dialysis fluid in the dialysis supply line being calculated when the filtration unit parameter relating to the efficiency of the filtration unit is newly determined during the extracorporeal blood treatment, and wherein calculating the updated value includes keeping the gradient substantially constant.

20. An apparatus for extracorporeal blood treatment comprising:

a filtration unit having a primary chamber and a secondary chamber separated by a semi-permeable membrane;

a blood circuit including a blood withdrawal line connected to an inlet of the primary chamber and a blood return line connected to an outlet of the primary chamber, said blood lines being configured for connection to a patient cardiovascular system;

a dialysis supply line connected to an inlet of the secondary chamber;

a dialysis effluent line connected to an outlet of the secondary chamber;

a preparation device configured to prepare a dialysis fluid, the preparation device connected to said dialysis supply line and comprising a regulator configured to regulate a composition of the dialysis fluid;

a sensor configured to measure a parameter value of a dialysate in the dialysis effluent line, said parameter value of the dialysate being at least one selected from the group consisting of a conductivity of the dialysate and a concentration of at least a substance in the dialysate; and a control unit in communication with the regulator and the sensor, the control unit configured to:

receive as input either: (i) an initial set point of the parameter value for the dialysis fluid in the dialysis supply line, wherein the control unit is configured to determine a gradient such that a value of a plasma conductivity or of a plasma concentration of at least a substance in the blood is achieved at an end of the extracorporeal blood treatment that tends to, or coincides with, the initial set point of the parameter value, or (ii) a desired value of the plasma conductivity or of the plasma concentration of at least a substance in the blood to be reached at the end of the extracorporeal blood treatment, wherein the control unit is configured to determine the gradient such that the desired value of the plasma conductivity or the plasma concentration of at least a substance in the blood is achieved at the end of the extracorporeal blood treatment;

set a parameter value for the dialysis fluid in the dialysis supply line at the initial set point, said parameter of the dialysis fluid being at least one selected from the group consisting of a conductivity of the dialysis fluid and a concentration of at least a substance in the dialysis fluid;

circulate, after setting the dialysis fluid parameter value at the initial set point, the dialysis fluid through the secondary chamber of the filtration unit;

circulate blood through the primary chamber of the filtration unit;

measure values of said parameter value of the dialysate downstream of said secondary chamber;

determine, by receiving, measuring or calculating, a filtration unit parameter relating to an efficiency of the filtration unit;

determine, by receiving, measuring or calculating, a plasma conductivity or a plasma concentration of at least a substance in the blood a plurality of times during the extracorporeal blood treatment;

calculate an updated value of the filtration unit parameter for the dialysis fluid in the dialysis supply line based on the parameter value of the dialysate in the dialysis effluent line, the parameter relating to the efficiency of the filtration unit, and the gradient between a current value of the parameter value for the dialysis fluid in the dialysis supply line and the plasma conductivity or the plasma concentration of at least a substance in the blood, wherein the updated value of the parameter for the dialysis fluid in the dialysis supply line is calculated when the plasma conductivity or the plasma concentration is newly determined during the extracorporeal blood treatment, wherein calculating the updated value includes keeping the gradient substantially constant; and command the regulator for regulating the composition of the dialysis fluid in the dialysis supply line at the updated value, wherein the gradient is defined as:

$$\Delta = (c_{di} - c_{bi})$$

or $$\Delta = (\kappa_{di} - \kappa_{bi})$$

wherein, $c_{di}$ s the concentration of at least a substance in the dialysis fluid at the inlet of the filtration unit, $c_{bi}$ is a concentration of at least a substance in the blood, $\kappa_{di}$ is the conductivity of the dialysis fluid at the inlet of the filtration unit, $\kappa_{bi}$ is the plasma conductivity, and wherein the gradient is defined either by a difference between conductivities or by a difference in concentrations.

* * * * *